(12) United States Patent
Morris et al.

(10) Patent No.: US 7,153,292 B2
(45) Date of Patent: *Dec. 26, 2006

(54) CATHETER FOR TARGET SPECIFIC DRUG DELIVERY

(75) Inventors: Mary M Morris, Mounds View, MN (US); Douglas Owen Hankner, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 276 days.

This patent is subject to a terminal disclaimer.

(21) Appl. No.: 10/828,688

(22) Filed: Apr. 21, 2004

(65) Prior Publication Data

US 2004/0199128 A1    Oct. 7, 2004

Related U.S. Application Data

(63) Continuation of application No. 09/625,751, filed on Jul. 26, 2000, now Pat. No. 6,945,969, which is a continuation-in-part of application No. 09/540,444, filed on Mar. 31, 2000, now Pat. No. 6,551,290.

(51) Int. Cl.
*A61M 5/00* (2006.01)
*A61M 25/00* (2006.01)

(52) U.S. Cl. .................... 604/246; 604/284; 604/93.01

(58) Field of Classification Search ................ 604/19, 604/48, 506–509, 511, 93.01, 94.01, 103.1, 604/118, 126, 173, 264, 523, 529, 284
See application file for complete search history.

(56) References Cited

U.S. PATENT DOCUMENTS

| 3,469,578 A | 9/1969 | Bierman |
|---|---|---|
| 3,640,269 A | 2/1972 | Delgado |
| 3,817,248 A | 6/1974 | Buckles et al. |
| 4,186,745 A | 2/1980 | Lewis et al. |
| 4,863,441 A | 9/1989 | Lindsay et al. |
| 4,947,842 A | 8/1990 | Marchosky et al. |
| 4,951,665 A | 8/1990 | Schneider |
| 4,968,306 A | 11/1990 | Huss et al. |
| 4,989,601 A | 2/1991 | Marchosky et al. |
| 5,087,244 A | 2/1992 | Wolinsky et al. |
| 5,181,659 A | 1/1993 | Ohe |
| 5,257,979 A | 11/1993 | Jagpal |
| 5,462,521 A | 10/1995 | Brucker et al. |

(Continued)

FOREIGN PATENT DOCUMENTS

EP    0 564 321    10/1993

(Continued)

*Primary Examiner*—Catherine S. Williams
(74) *Attorney, Agent, or Firm*—Mary P. Bauman

(57) ABSTRACT

A medical catheter comprising a proximal end having an opening for fluid containing a therapeutic drug, a distal end, the distal end defining at least one opening, and a porous portion covering the opening defined by the distal end. In one embodiment, the medical catheter comprises a proximal end having an opening for fluid containing a therapeutic drug, at least two distal ends, the proximal end connected to the two distal ends with a connector, the distal ends each defining at least one opening, a diffuser covering the opening of each distal end, and a separate restrictor downstream of the connector and upstream of each distal end to provide substantially equal flow through each distal end. An additional restrictor can also be placed upstream of the connector. In another embodiment, a combination diffuser and restrictor covers the opening of each distal end. In one embodiment, the diffuser can define tubes that extend from the inside surface of the diffuser to the outside surface of the diffuser, to permit more equal drug flow through the tubes defined therein.

62 Claims, 12 Drawing Sheets

U.S. PATENT DOCUMENTS

| | | |
|---|---|---|
| 5,695,479 A | 12/1997 | Jagpal |
| 5,782,797 A | 7/1998 | Schwiech, Jr. et al. |
| 5,810,760 A | 9/1998 | Andrews |
| 5,823,996 A | 10/1998 | Sparks |
| 5,846,220 A | 12/1998 | Elsberry |
| 5,848,987 A | 12/1998 | Baudino et al. |
| 5,858,003 A | 1/1999 | Atala |
| 5,957,901 A | 9/1999 | Mottola et al. |
| 6,017,323 A | 1/2000 | Chee |
| 6,030,358 A | 2/2000 | Odland |
| 6,050,986 A | 4/2000 | Hektner |
| 6,056,725 A | 5/2000 | Elsberry |
| 6,093,180 A | 7/2000 | Elsberry |
| 6,171,298 B1 | 1/2001 | Matsuura et al. |
| 6,241,710 B1 | 6/2001 | Van Tassel et al. |
| 6,551,290 B1 * | 4/2003 | Elsberry et al. ............ 604/284 |

FOREIGN PATENT DOCUMENTS

| | | |
|---|---|---|
| JP | 3-41967 | 2/1991 |
| WO | WO 96/33761 | 10/1996 |
| WO | WO 98/15315 | 4/1998 |

* cited by examiner

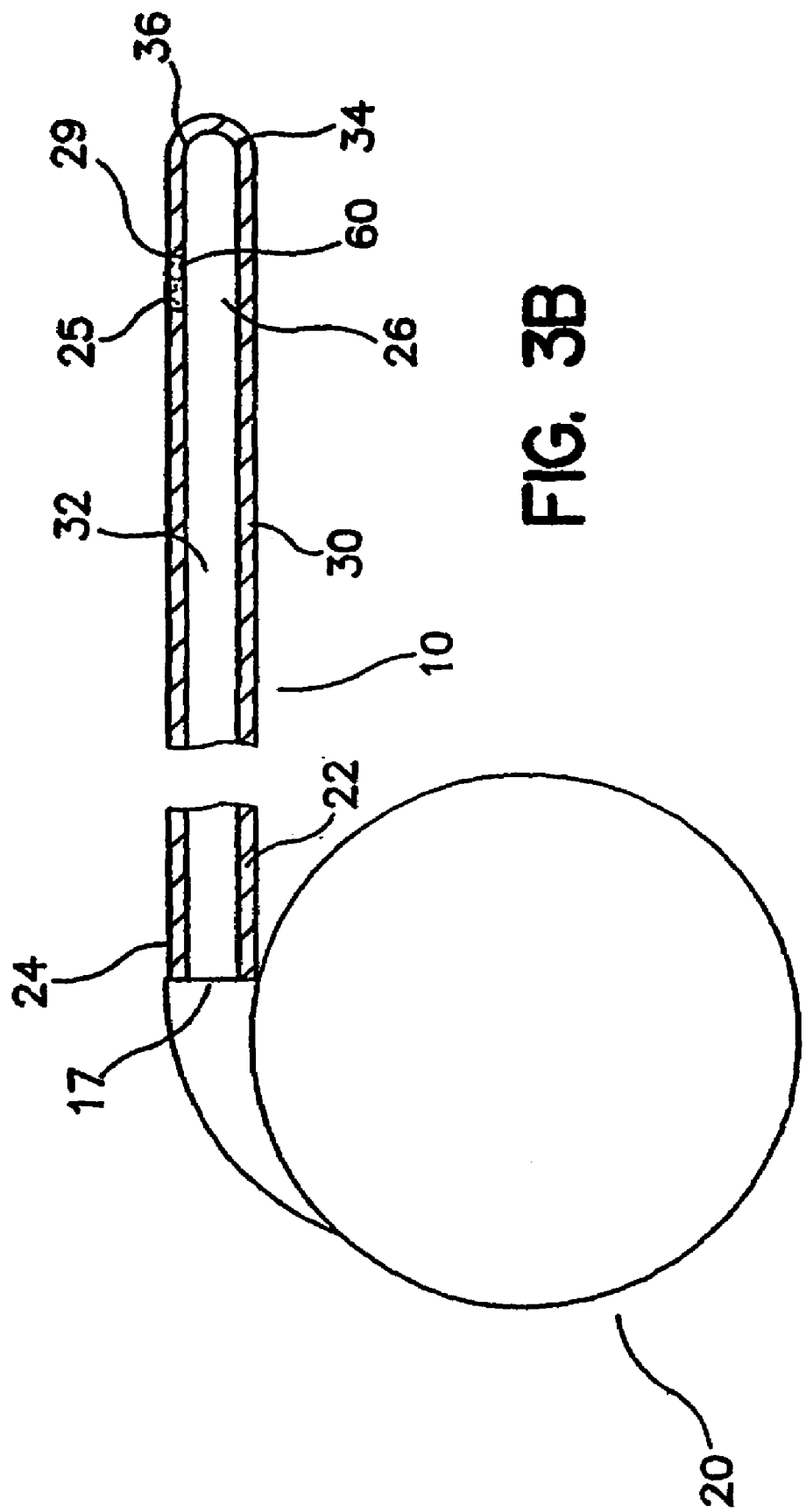

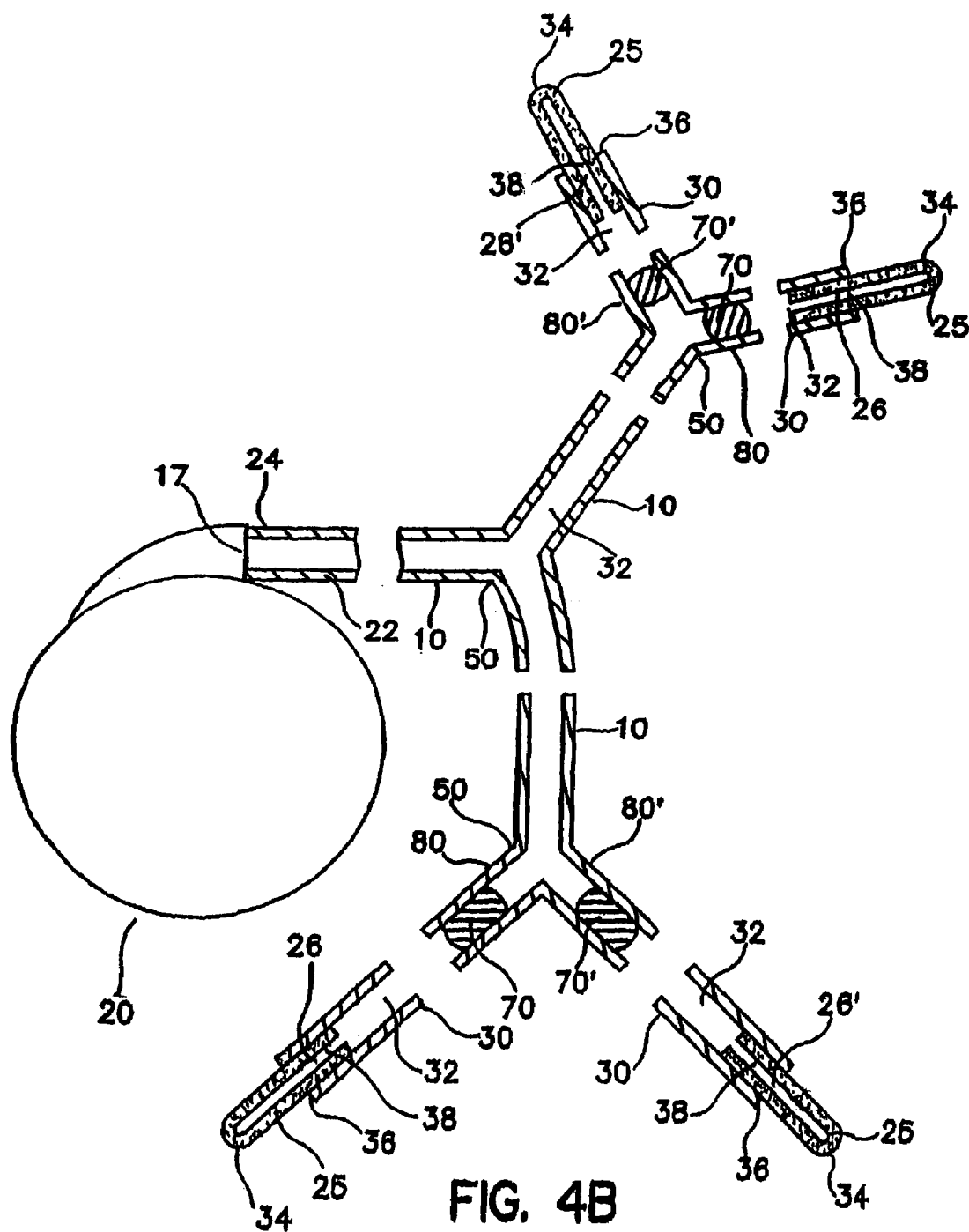

CATHETER FOR TARGET SPECIFIC DRUG DELIVERY

CROSS-REFERENCE TO RELATED APPLICATION

This application is a continuation of U.S. Ser. No. 09/625,751, filed Jul. 26, 2000 now U.S. Pat. No. 6,945,969, which is a continuation-in-part of U.S. Ser. No. 09/540,444, filed Mar. 31, 2000 now U.S. Pat. No. 6,551,290, both of which are incorporated herein by reference in their entireties.

FIELD OF INVENTION

This invention relates to medical catheters for target specific drug delivery.

BACKGROUND OF THE INVENTION

Medical therapies may require the targeting of the therapy to a targeted patient site to maximize the therapeutic benefit and/or minimizing adverse effects to other organs or tissues outside the targeted patient site.

Huss & Reinhardt, U.S. Pat. No. 4,968,306 describes an elongated catheter assembly for intravascular delivery of intravenous therapeutic fluids. This assembly has a distal end having multiple pores which is sheathed by an outer proximal segment for variable exposure of delivery surface area by sliding the distal segment from the outer proximal sheath. A disadvantage of this assembly is that it results in a lack of homogeneity of pore placement and pore number for fluid discharge, which indicates a pore size of 2–20 microns.

Delgado, U.S. Pat. No. 3,640,269 describes a fluid delivery assembly having two flexible fluid-impermeable tubes open at one end and provided with an enlarged flexible permeable bag at the delivery segment. This bag is comprised of a membrane having uniform porosity less than 0.5 microns and having a water permeability of at least 60 mL/minute/cm as a description of fluid permeability. While this design is capable of uniform fluid delivery to tissues adjacent to the permeable bag, a disadvantage of this assembly is its inability to be specifically targeted to a patient site due to the flexible distal bag.

Thus, there is a need for a device that provides uniform distribution of therapeutic agents to a targeted patient site or multiple targets sites. There is also a need for a device that provides this uniform distribution, yet has sufficient rigidity for accurate placement of the device so that it can deliver therapeutic agents to the targeted patient site or multiple sites.

SUMMARY OF THE INVENTION

A new medical catheter has now been discovered that provides uniform distribution of therapeutic agents to a targeted patient site. Moreover, the medical catheter of the present invention has a unique structure that permits it to be accurately placed so that it can uniformly distribute therapeutic agents to the targeted patient site.

In a one embodiment of the present invention, the catheter has at least two distal ends, and a proximal end joined to the two distal ends via a connector, such as a "Y" connector having three legs. Thus, the two distal ends and the proximal end are each located at a separate ends of the legs of the connector. Preferably, restrictors are placed in each leg of the connector. A restrictor is a structure that provides a significant pressure drop when fluid flows through that structure. The restrictors of the present invention provide structure to balance the flow for a multiple catheter system. The restrictors can be made of any suitable material, e.g. a powder material such as sintered metal powder. In this embodiment, diffusers are placed at the distal ends. A diffuser is a structure that diffuses and delivers a therapeutic agent over a large surface area as opposed to a single point source. In this embodiment, the diffusers and restrictors, which are in each leg having a distal end, are separated from each other. Preferably, the diffuser is at the tip of each distal end, and the each restrictor is upstream of the distal end. This construction is particularly useful for delivery of drugs via multiple catheter ends. For example, drug delivery to the two different hemispheres of the brain may be achieved, and the present invention can deliver drugs to each hemisphere substantially equally because of the restrictor(s) upstream of the distal ends, rather than at the distal ends as are the diffusers. In this embodiment of the present invention the following benefits are obtained by separating the diffuser and the restrictor: (1) increase in design options for the catheter tip; (2) improved reliability of catheter tip that is implanted in the brain tissue; and (3) reduced need to test the restrictor structure for biostability.

In another embodiment of the present invention, a restrictor is placed upstream of the Y connector as well, so that there is a restrictor in all three legs of the catheter joined by the Y connector. This construction provides additional benefits. For example, having the restrictor upstream of the Y connector acts as a pre-filter, and thus removes any particulates prior to the Y connector. This pre-filter function reduces particulates to the restrictors downstream of the Y connector, thus reducing the potential for different pressure drops and flow rates through the restrictors downstream of the Y connector, and ultimately the flow rate of the delivered drug through the diffusers at the distal ends. In addition, this embodiment eliminates the possibility for insertion of a catheter where only one restrictor is downstream of the Y connector, and one restrictor is upstream of the Y connector.

In another embodiment, the catheter of the present invention comprises a rigid assembly having a rigid tube for positioning the distal end of the catheter near a targeted patient site or sites, the distal end of the catheter has a rigid porous delivery segment having a porosity less than 0.50 microns for achieving homogenous delivery to the targeted patient site. More specifically, in this embodiment, the catheter of the present invention has a rigid assembly having an open tube having a distal end, the distal end having sintered metal powder, for example, metal microspheres to provide uniform porosity of the delivery segment. In this embodiment, the distal end comprises at least one uniform surface made of sintered metal powder. Preferably, the sintered metal powder can be made of any light-weight, high tensile strength material, e.g., tungsten, titanium or tantalum. In this embodiment, the rigid assembly functions as both a diffuser and a restrictor. The sintered metal rigid assembly of this embodiment can be fabricated using a single cavity carbon mold, and a mold insert. Alternatively, the sintered metal rigid assembly can be fabricated using powdered metal and pyrogenic sintering, such as high pressure plus pyrogenic sintering. Sintered metal rigid assemblies can be positioned at the distal ends of separate legs of a catheter for placement at multiple patient targets. The distal ends can each join to a connector (e.g., a "Y" connector) for connection to a single therapy source. The sintered metal rigid assembly of this embodiment functions as both a fluid restrictor and a fluid diffuser. Thus, the diffuser and restrictor functions can be combined, as in a membrane tip, or separated, with the restrictor being upstream of the diffuser in each leg of the catheter.

When it is desired for the sintered metal powder to be radiopaque, a radiopaque material can be used, such as tungsten, titanium or tantalum. These metals are non-magnetic, and therefore are safe within a magnetic imaging environment.

An objective of the present invention is to provide for multiple catheter ends for drug delivery arising from a single pump source. The present invention provides a catheter construction that provides desired distribution in a targeted area of the patient, such as giving medications intraparenchymally into tissue. Drug delivery by the present invention can be to an organ, and uniform distribution to that organ may be desired. It is a further objective of the present invention to provide for multiple catheter ends, at least two, into the brain of patient, and more specifically, into the two different hemispheres of the brain, with each catheter end supplied with therapeutic drugs by the same pump, and with the fluid flow of the therapeutic agent being substantially equal between the two catheter ends. It is usually desirable to have equal amounts of drug delivered to both brain hemispheres.

Another objective of the present invention is to provide a catheter to diffuse a therapeutic agent over a larger surface area than from a single point source. This structure results in a decrease in fluid flux and reduces potential for damaging tissue near the infusion site. In order for equal or near equal bilateral drug delivery to occur, two distal ends are required since fluid delivered from one distal end to a target site at one hemisphere will not deliver fluid to the other hemisphere.

The present invention can be used for many drug delivery applications, including but not limited, to intraparenchymal or tissue infusion (such as brain tissue infusion), intrathecal drug delivery and intracerebral ventricular (ICV) drug delivery, or any drug infusion into a fluid filled space or to a tumor.

BRIEF DESCRIPTION OF THE DRAWINGS

FIG. 3B illustrates another embodiment of the catheter of the present invention in combination with device 20.

FIG. 4B illustrates another embodiment of the present invention in combination with device 20, this embodiment having multiple connectors 50, and multiple diffuser distal catheter segments with separate restrictors placed between each diffuser distal catheter segment and a corresponding connector 50.

DESCRIPTION OF THE PREFERRED EMBODIMENTS

Figure 1:
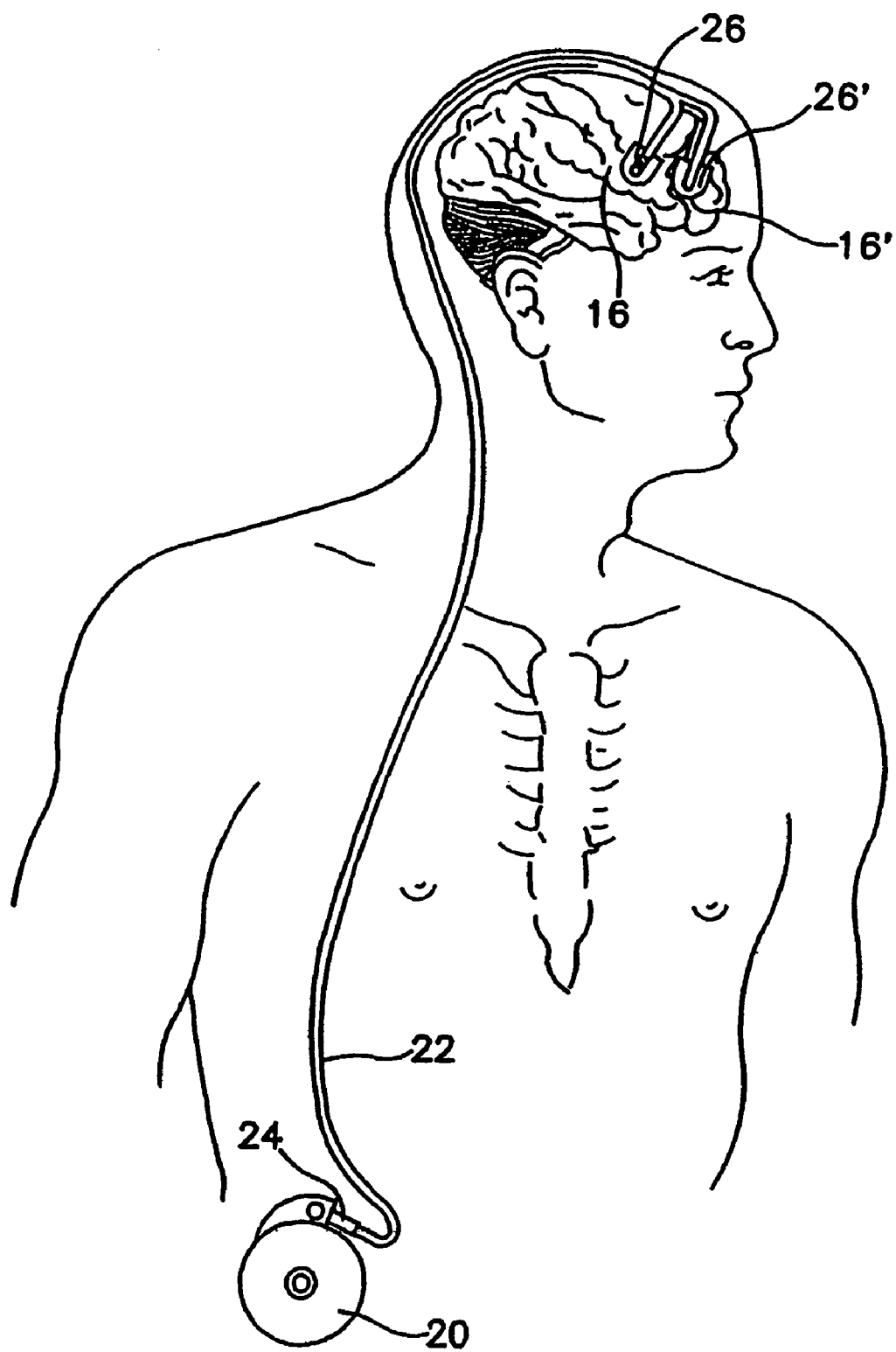
FIG. 1 illustrates the catheter of the present invention, as implanted in a preferred location of the human body, and for drug delivery to each side of a patient's brain.
Figure 2:
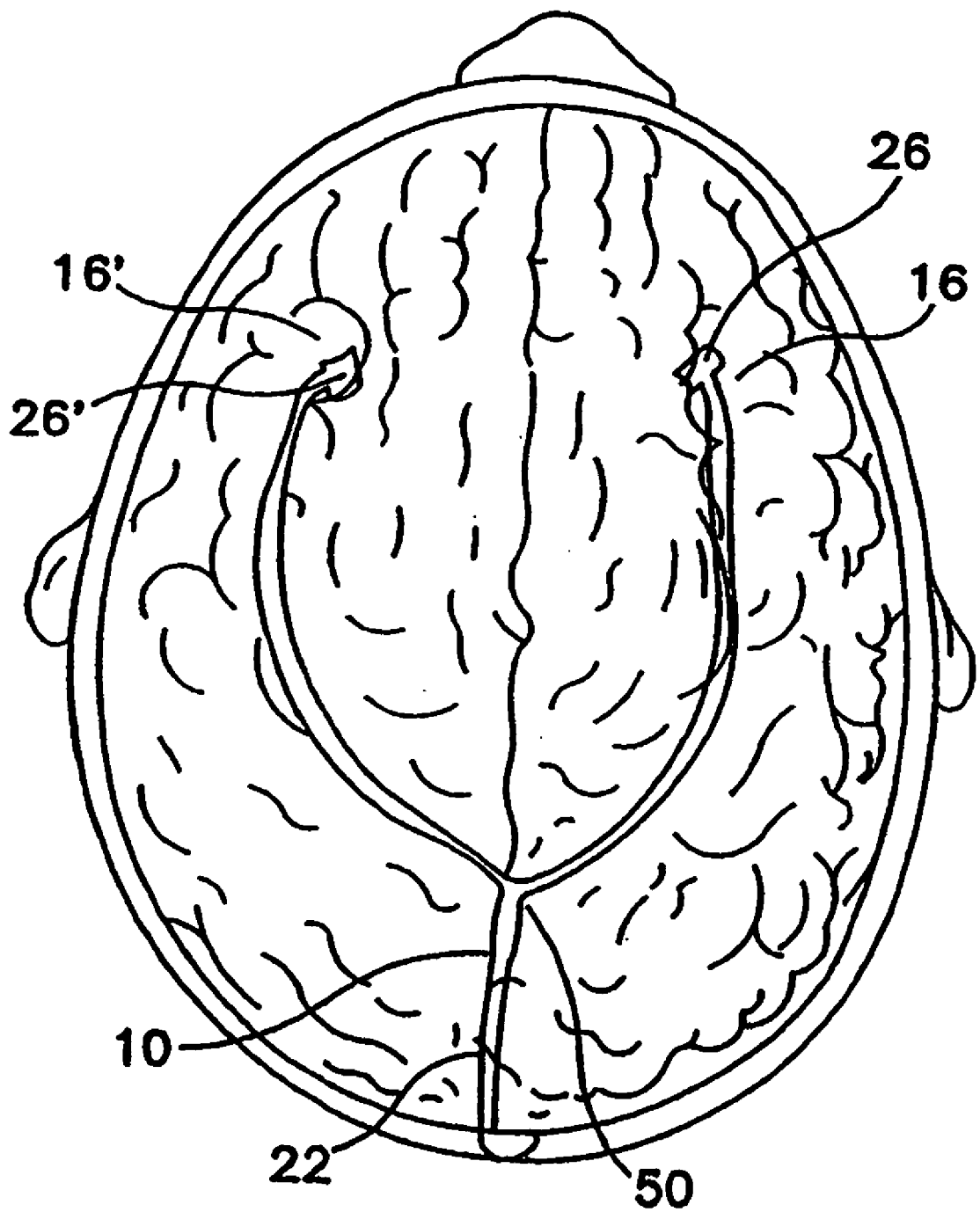
FIG. 2 is a top view of the catheter of the present invention as implanted and which provides drug delivery to the two hemispheres of a patient's brain.

As shown in FIGS. 1 and 2, in an embodiment of the present invention, catheter 22 has a proximal end 24, and distal ends 26 and 26'. Distal ends 26 and 26' are connected to catheter 22, which splits at a "Y" connector 50. Distal end 26 is positioned in the right anterior cerebral cortex 16, and distal end 26' is positioned in the left anterior cerebral cortex 16'. Proximal end 24 is attached device 20, which can be an implantable infusion pump. While two distal ends are shown, the present invention can have one or more than two distal ends.

As further shown in the embodiment depicted in FIG. 2, catheter 22 has a catheter portion 10 downstream of device 20 and upstream of connector 50.

Combined Diffuser/Restrictor

Figure 3A:
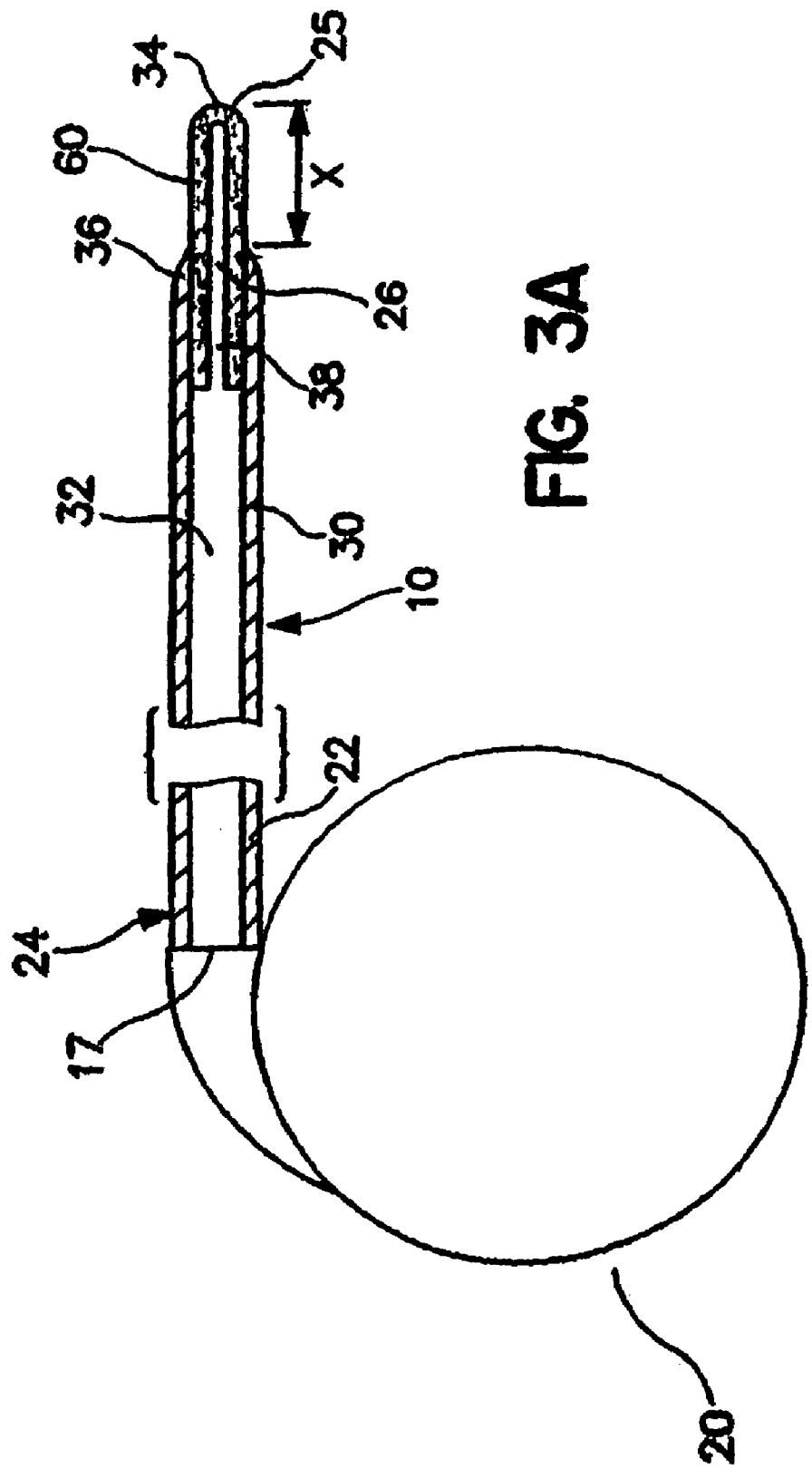
FIG. 3A illustrates an embodiment of the catheter of the present invention in combination with device 20.

As shown in FIG. 3A, where there is only one distal end 26, and there is no connector 50. Catheter portion 10 preferably comprises an elongated tubular wall 30 defining a central lumen 32. In this embodiment, catheter 22 begins at proximal end 24 and terminates at distal end 26. In this embodiment, distal end 26 has a catheter tip 34. Proximal end 24 defines an opening 17. Lumen 32 is defined by tubular wall 30. Tubular wall 30 terminates at end 36. In this embodiment, catheter tip 34 is attached to tubular wall 30. Catheter tip 34 has a lumen 38 to receive a drug from lumen 32, which can receive a drug pumped from device 20. Tubular portion 30 ends at end 36. Throughout this disclosure, the length of the portion of catheter tip 34 that is exposed to patient tissue is represented by a distance "x".

In this embodiment, catheter 22 of the present invention comprises a rigid assembly having a rigid tubular wall 30 for positioning the distal end 26 of the catheter 22 near a targeted patient site, the distal end 26 having a rigid porous portion or drug delivery segment 60 made of a sintered microsphere material having a porosity less than 0.50 microns for achieving homogenous delivery to the targeted patient site. In this embodiment, rigid porous drug delivery segment 60 comprises sintered metal microspheres to provide uniform porosity. Thus, a drug can be pumped from device 20, through opening 17, through lumen 32, through lumen 38, and through porous drug delivery segment 60 to a targeted patient site. In the embodiment shown in FIG. 3A, delivery segment 60 can also be referred to as a combination diffuser and restrictor. In other words, delivery segment 60 restricts flow of a fluid containing a therapeutic drug and also diffuses that fluid so that the fluid is distributed to and emitted from the outer surface of delivery segment 60 that is exposed to a targeted patient site.

In this embodiment, the sintered metal powder of the delivery segment 60 defines multiple pores or porous openings 25. Preferably, the sintered metal powder is made of any light-weight, high tensile strength material, e.g., tungsten, titanium or tantalum.

The sintered rigid metal assemblies can be fabricated using a single cavity carbon mold, and a mold insert. Alternatively, the rigid metal assembly can be pressed into a green part using high pressure and sintered using heat to convert the green part to a fused structure (i.e, without carbon molds). Microspheres can be compressed together in each mold with pyrogenic processing.

When it is desired for the sintered metal powder to be radiopaque, a radiopaque material can be used, such as tungsten, titanium or tantalum. These metals are non-magnetic, and therefore are safe within a magnetic imaging environment.

The desired porosity of the sintered porous tip can be selected upon the diameter of the metal powder spheres used in the mold fabrication process. In this embodiment, the maximal dimensional distance between adjacent microspheres (i.e., pore size) is directly related to microsphere diameter, and is preferably as follows:

| Mircrosphere Diameter | Maximal Dimensional Distance (i.e. Pore Size) |
| --- | --- |
| 40 microns | Less than 6.2 microns |
| 30 microns | Less than 4.7 microns |
| 20 microns | Less than 3.1 microns |
| 10 microns | Less than 1.6 microns |
| 5 microns | Less than 0.8 microns |
| 3 microns | Less than 0.5 microns |
| 2 microns | Less than 0.3 microns |

In actual practice, the maximal dimensional space is less than ideal since compression during the sintering process reduces dimension.

In U.S. Pat. No. 5,846,220 (assigned to Medtronic), which is incorporated herein by reference, a therapeutic method for treatment of Alzheimer's disease is disclosed. In U.S. Pat. No. 5,846,220, the distal end has a porous tip or a closed end, wherein the catheter tip is preferably composed of porous material such as polysulfone hollow fiber, manufactured by Amicon, although polyethylene, polyamides, polypropylene and expanded polytetrafluoroethlyene (ePTFE) are also suitable, and is preferable porous along its entire length to enable indomethacin to flow into the hippocampus, and the preferred pore size is approximately ranged between 0.1–0.2 microns. See Col. 5, line 64 through Col. 6, line 4 of U.S. Pat. No. 5,846,220.

The present invention differs from U.S. Pat. No. 5,846,220, because, among other things, the present invention has much larger pore sizes, i.e., about 0.3 to 6.2 microns, and the porous material in the present invention is preferably made from sintered metal microspheres.

Another embodiment is shown in FIG. 3B. This embodiment is similar to FIG. 3A, except that there is a side opening 29 defined in distal end 26, and delivery segment 60 is positioned at side opening 29. Alternatively, delivery segment 60 can be positioned over or under side opening 29, relative to tubular wall 30. Side opening 29 can be incorporated into other embodiments shown and/or described herein.

Figure 3C:
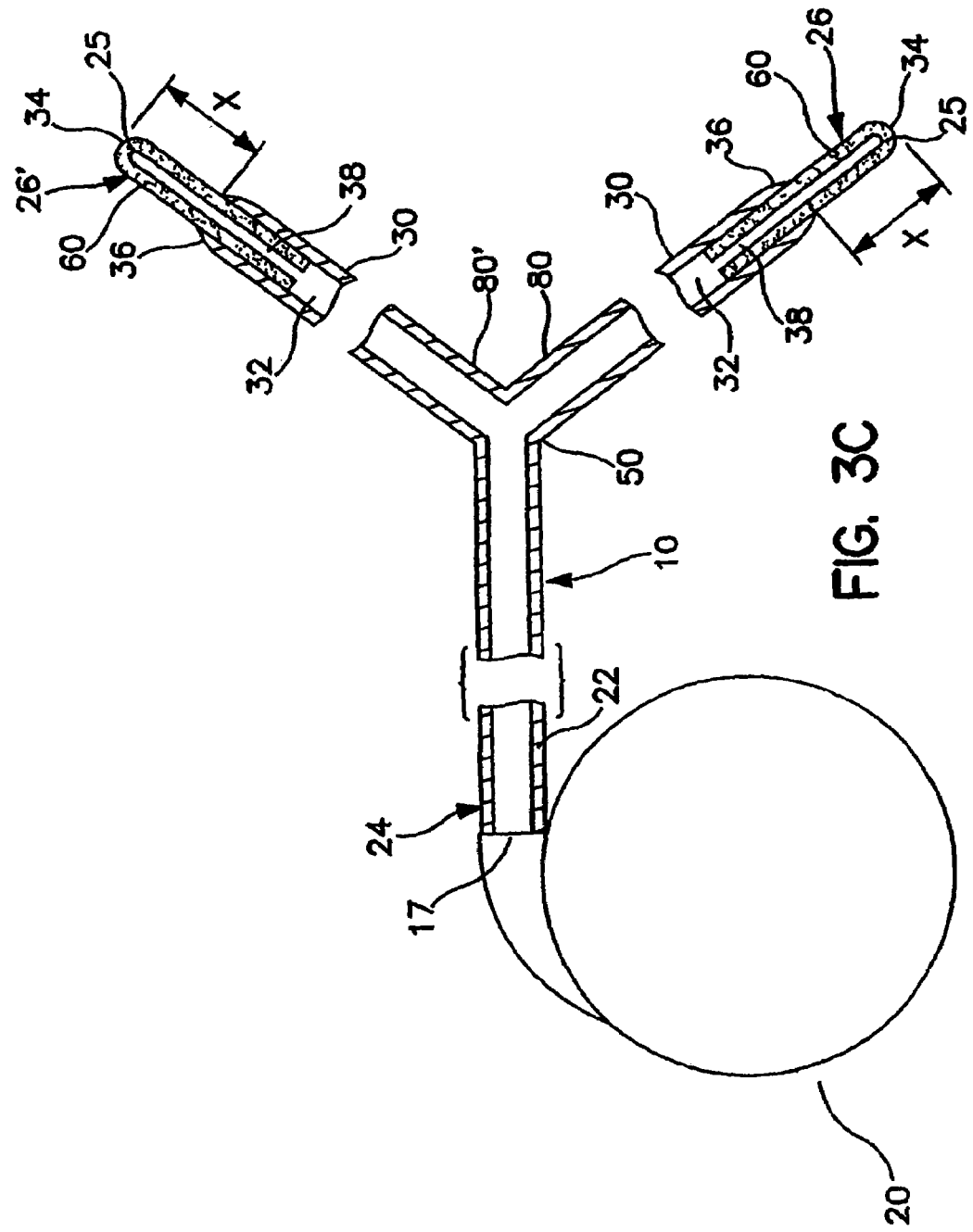
FIG. 3C illustrates another embodiment of the catheter of the present invention in combination with device 20, this embodiment having two diffuser and restrictor distal catheter segments.

Another embodiment is shown in FIG. 3C. FIG. 3C is similar to FIG. 3A, except there are two distal ends, 26 and 26', two drug delivery segments 60, and two legs 80 and 80' connected to a connector 50 and corresponding distal ends 26 and 26'. This embodiment can be referred to as a catheter having two diffuser/restrictor catheter segments. This embodiment can be used to deliver a drug to two targeted patient sites.

Figure 3D:
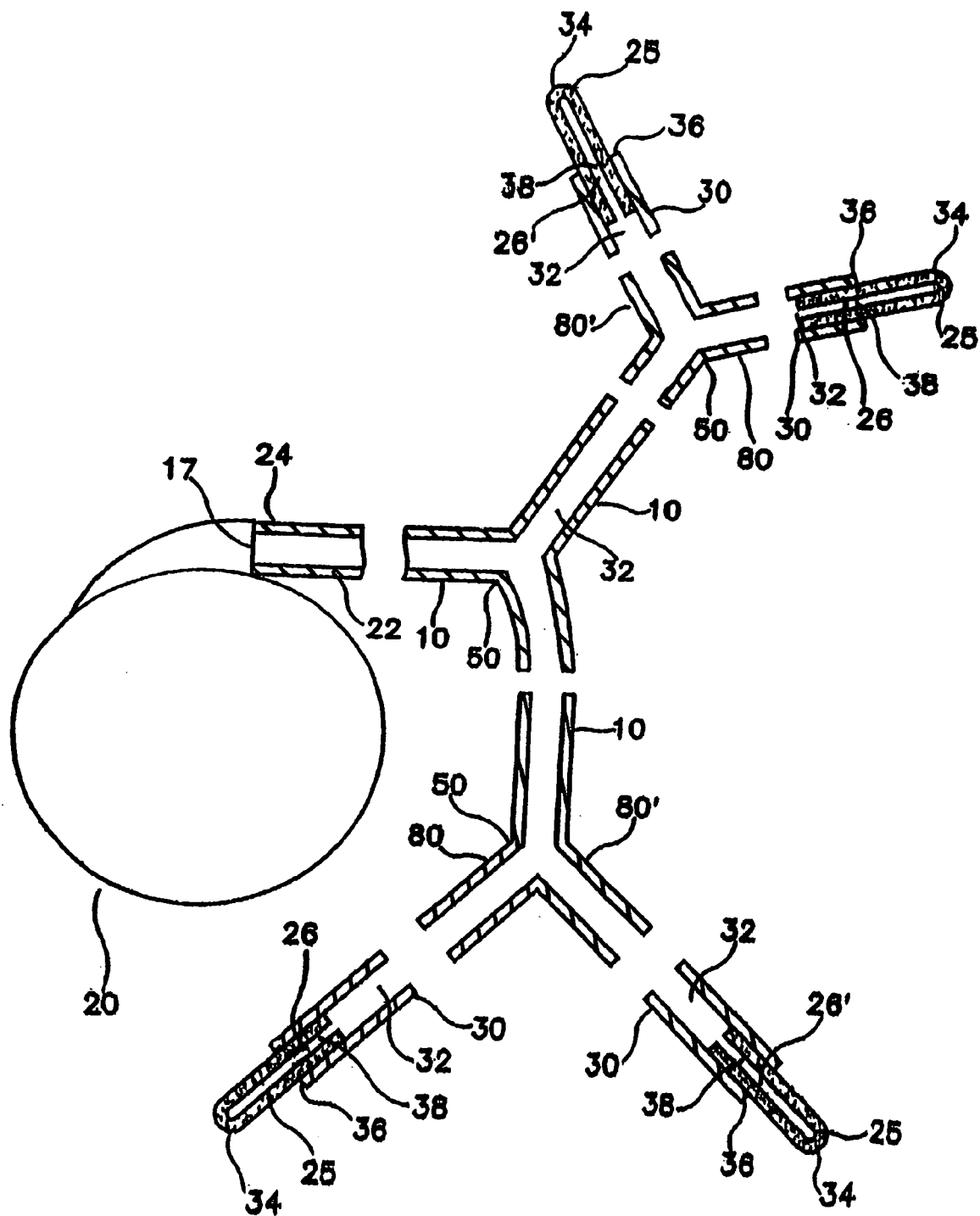
FIG. 3D illustrates another embodiment of the present invention in combination with device 20, this embodiment having more than two diffuser and restrictor distal catheter segments.

An alternative embodiment is shown in FIG. 3D. This embodiment is the same as that shown in FIG. 3C, except that there are more than one connector 50, and more than two distal ends (in this embodiment, two distal ends 26 and two distal ends 26', for a total of four distal ends), more than two delivery segment portions 60, more than one catheter portion 10, and more than two distal tips 34 having lumens 38 to receive a drug from lumens 32. While four distal ends are shown, the present invention can have any number of distal ends as may be desired for drug delivery to targeted patient sites. Connectors 50 are used to connect the proximal end 24 to catheter portions 10 and catheter portions 10 to legs 80 and 80'. This embodiment can be referred to as catheter having multiple diffuser/restrictor catheter segments. This embodiment can be used to deliver a drug to more than two patient sites.

Separate Diffuser and Restrictor

Figure 4A:
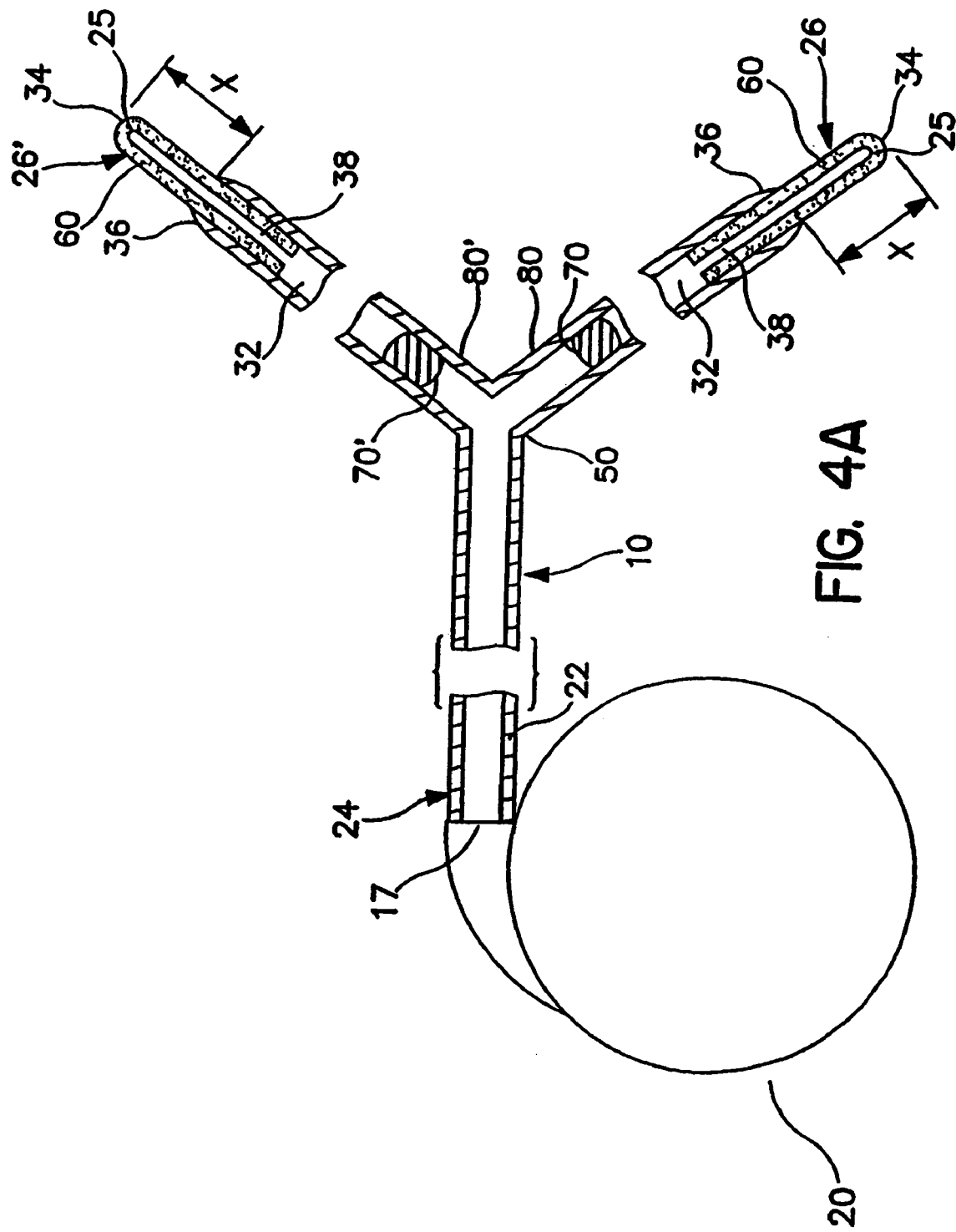
FIG. 4A illustrates another embodiment of the catheter of the present invention in combination with device 20, this embodiment having a separate restrictor placed between each diffuser distal catheter segment and connector 50.

Another embodiment of the present invention is shown in FIG. 4A. This embodiment has many of the same elements previously described for other embodiments, and in particular, the embodiment shown in FIG. 3C. The embodiment shown in FIG. 4A has a catheter 22 having at least two distal ends 26 and 26', and catheter portion or leg 10 joined to each distal end with a connector 50. Further, restrictors 70 and 70' are placed in each legs 80 and 80', which are downstream of connector 50. Restrictors 70 and 70' can be made of any suitable material, including but not limited to, e.g. sintered metal powder, which is previously described above, or a material that provides a small diameter fluid path or capillary tubes. In this embodiment, the drug delivery segment (i.e., diffuser) 60 and restrictors 70 and 71' are separated from each other. The drug delivery segment 60 is at tip 34 of each of the distal ends 26 and 26', and the restrictors 70 and 71' are upstream of distal ends 26 and 26', respectively. This construction is particularly useful for delivery of drugs via multiple (more than one) catheter ends. For example, drug delivery to the two different hemispheres of the brain may be desired, and the present invention can deliver drugs to each hemisphere substantially equally because of the restrictors upstream of the distal ends, rather than at the distal ends as are the diffusers. In this embodiment of the present invention the following benefits are obtained by separating the diffuser and the restrictor: (1) increase in design options for the catheter tip; (2) improved reliability of catheter tip that is implanted in the brain tissue; and (3) reduced need to test the structure of the restrictor for biocompatibility.

An alternative embodiment is shown in FIG. 4B. This embodiment is the same as that shown in FIG. 4A, except that there is more than one connector 50, more than two distal ends (in this embodiment, two distal ends 26, and two distal ends 26' for a total of four distal ends), more than two delivery segment portions 60, more than one catheter portion 10, more than one leg 80, more than one leg 80', and more than two distal tips 34 having a lumen 38 to receive a drug from lumen 32. The connectors 50 are used to connect catheter portions 10 to the proximal end 24. This embodiment can be used to deliver a drug to more than two targeted patient sites.

Figure 5A:
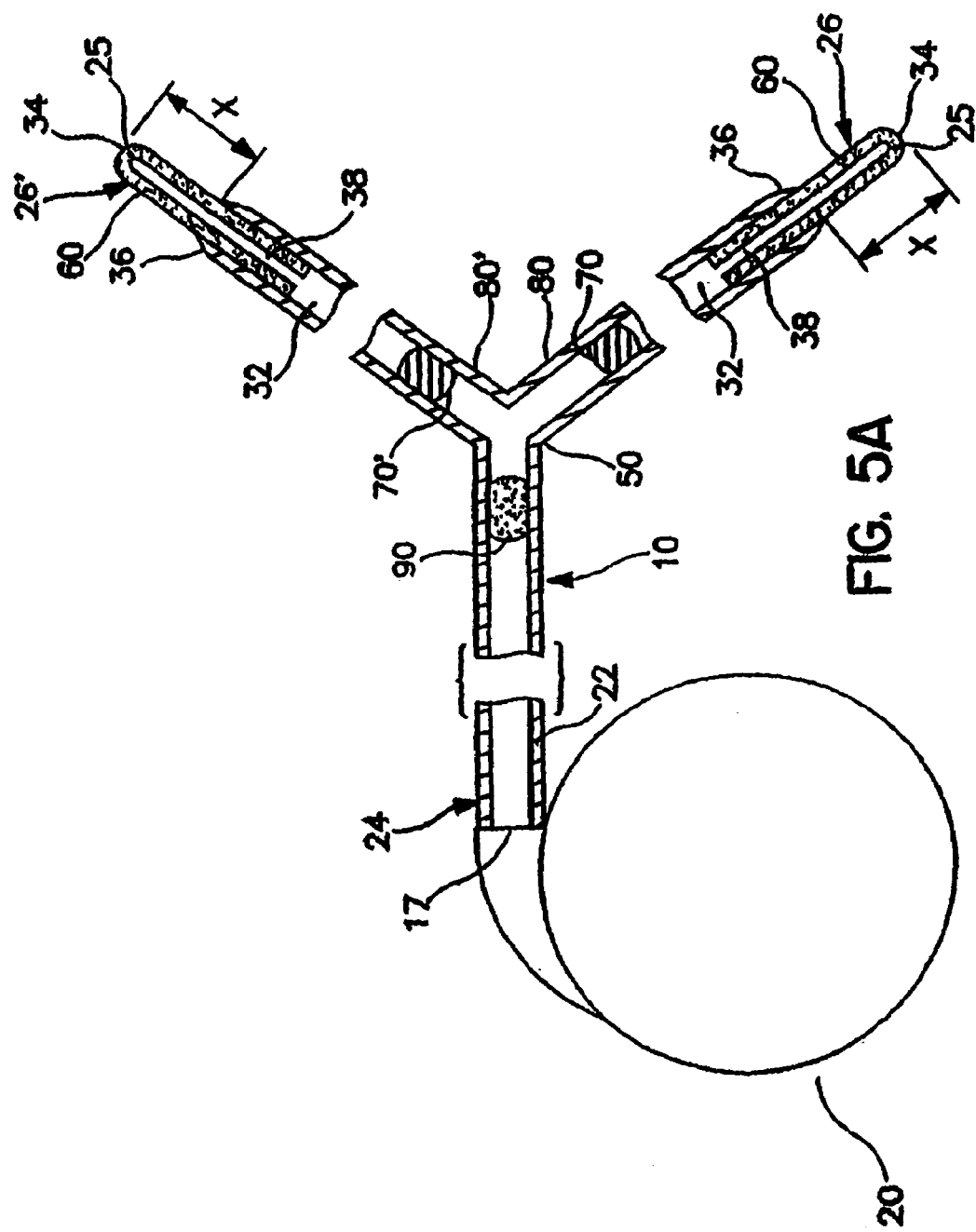
FIG. 5A illustrates another embodiment of the catheter of the present invention in combination with device 20, this embodiment having separate restrictors placed between each diffuser distal catheter segment and a corresponding connector 50, and a restrictor 90 placed between proximal end 24 and the first connector 50 downstream of proximal end 24.

FIG. 5A shows the same structure as FIG. 4A, except that in this other embodiment of the present invention, a restrictor 90 is placed upstream of connector 50 as well, so that there is a restrictor in legs 80, 80' and catheter portion 10 of the catheter 22 joined by connector 50. This construction provides additional benefits. For example, having the restrictor 90 upstream of the connector 50 acts as a pre-filter, and thus removes any particulates prior to connector 50. This pre-filter function reduces particulates to the restrictors 70 and 70' downstream of connector 50, thus reducing the potential for different pressure drops and flow rates through the restrictors 70 and 70' downstream of connector 50, and ultimately the flow rate of the delivered drug through the diffusers or delivery segments 60 at the distal ends. In addition, this embodiment eliminates the possibility for incorrect insertion of a catheter where only one restrictor is downstream of connector, and one restrictor is upstream of connector 50, and one leg 80 or 80' not having a restrictor.

Figure 5B:
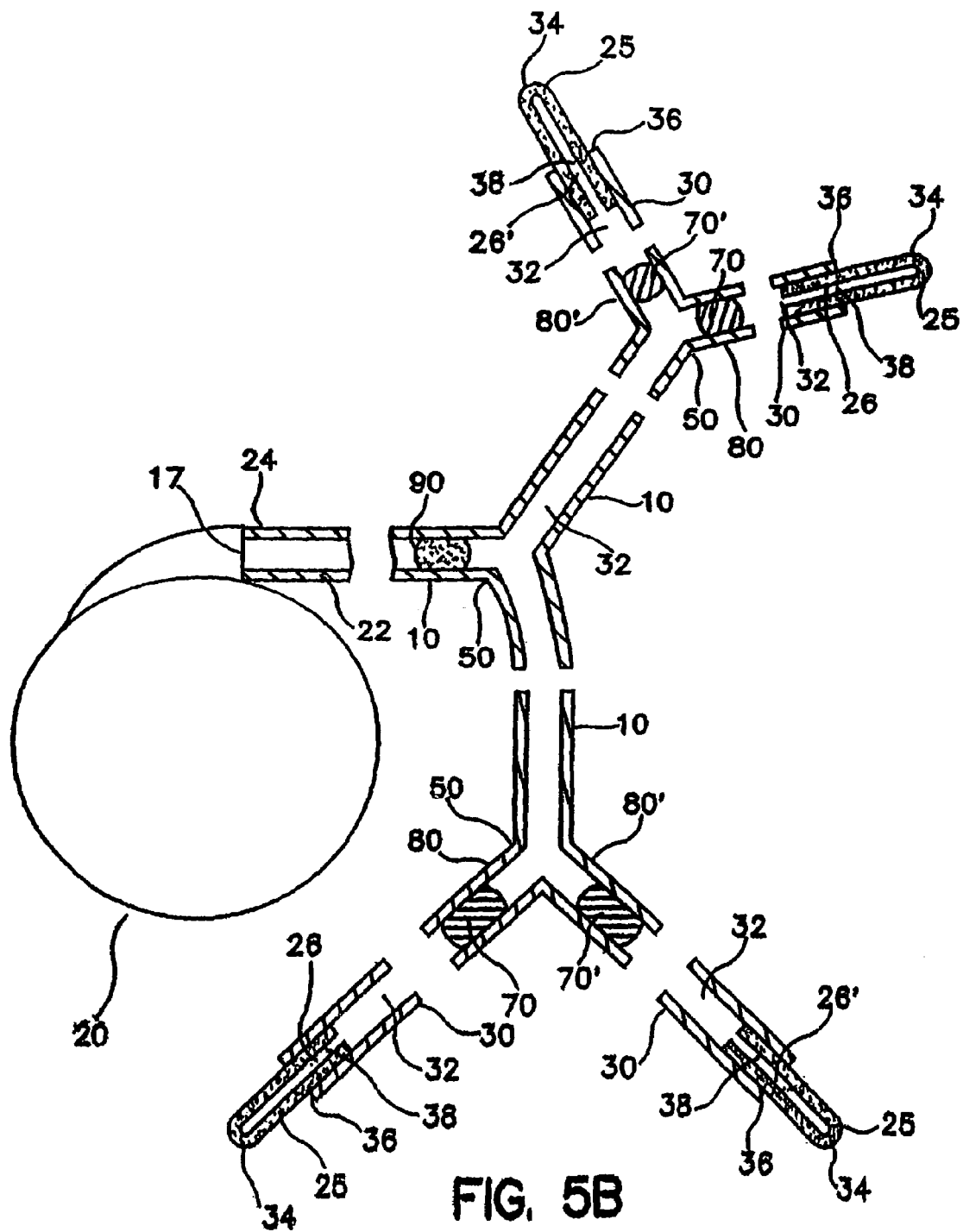
FIG. 5B shows the same structure as FIG. 4B, except that in this other embodiment of the present invention, a restrictor 90 is placed between proximal end 24 and the first connector 50 downstream of proximal end 24.

FIG. 5B shows the same structure as FIG. 4B, except that in this other embodiment of the present invention, a restrictor 90 is placed between proximal end 24 and the first connector 50 downstream of proximal end 24, to deliver a drug to more than two targeted patient sites.

In accordance with the embodiments shown in FIGS. 4A, 4B, 5A, and 5B, the drug fluid is pushing through many small pores of the drug delivery segment 60, and restrictors 70, 70' and 90 are of substantially equal flow resistance, and thus the delivered drug fluid follows a tortuous path. In these embodiments, the sum of the resistance to flow through multiple catheter distal ends is preferably equal so that equal flow is through the multiple catheter distal ends is obtained. The structures described above and shown in FIGS. 4A, 4B, 5A, and 5B provide substantially equal flow through multiple catheter distal ends. Further discussion about the drug delivery segment (i.e. diffuser) and the fluid restrictor is set forth below.

Fluid Diffuser—Fluid modeling reveals that distribution of fluid flow will occur with multiple small holes in simple silicone or polyurethane catheters. The diffuser, i.e., the drug delivery segment 60 shown in FIGS. 4A, 4B, 5A and 5B, can comprise any suitable structure. For example, the diffuser can comprise material having laser drilled holes or tubes having 0.001–0.005 inches (i.e., 0.0025–0.0127 cm) diameter, and about 20–100 holes per diffuser. In one embodiment, the most distal of forty holes having 0.005 inches (0.0127 cm) in diameter should have 76% of the flow compared to the most proximal hole (total flow 1 microliters/minute). For holes that are 0.001 inches (0.0025 cm) in diameter, the distal hole should have 99.95% of the flow compared to the proximal hole. In addition, many porous materials such as sintered metal, sintered polyethylene, or porous PTFE (i.e., Teflon) have diffuser capability. Thus, these structures are good diffusers at flow rates of about 1 microliter/minute to about 20 microliters/minute. For the diffuser material, a permeability constant of less than about 30,000 and a bubble point of less than about 10 psi is preferred.

As previously noted, the drug delivery segment can be made of any light-weight, high tensile strength material, e.g., tungsten, titanium or tantalum. Further, the drug delivery segment can be made of any suitable radiopaque material (e.g., tantalum, tungsten, titanium, gold, platinum, iridium, silver, nickel, and alloys thereof).

Suitable radiopaque material can be placed in any suitable portion of the medical catheter of the present invention, and is not limited to the drug delivery segment. Thus, the medical catheter of the present invention may include at least one portion comprising a radiopaque material from the group consisting of tantalum, tungsten, titanium, gold, platinum, iridium, silver, nickel and alloys thereof. Incoporation of a portion or marker, such as a band or bead, having radiopaque material can enable medical personnel to identify the location of the catthether and drug delivery segment within a patient, via X-ray, magnetic resonance imaging (MRI), and/or computerized axial tomography (CAT scan).

Figure 6:
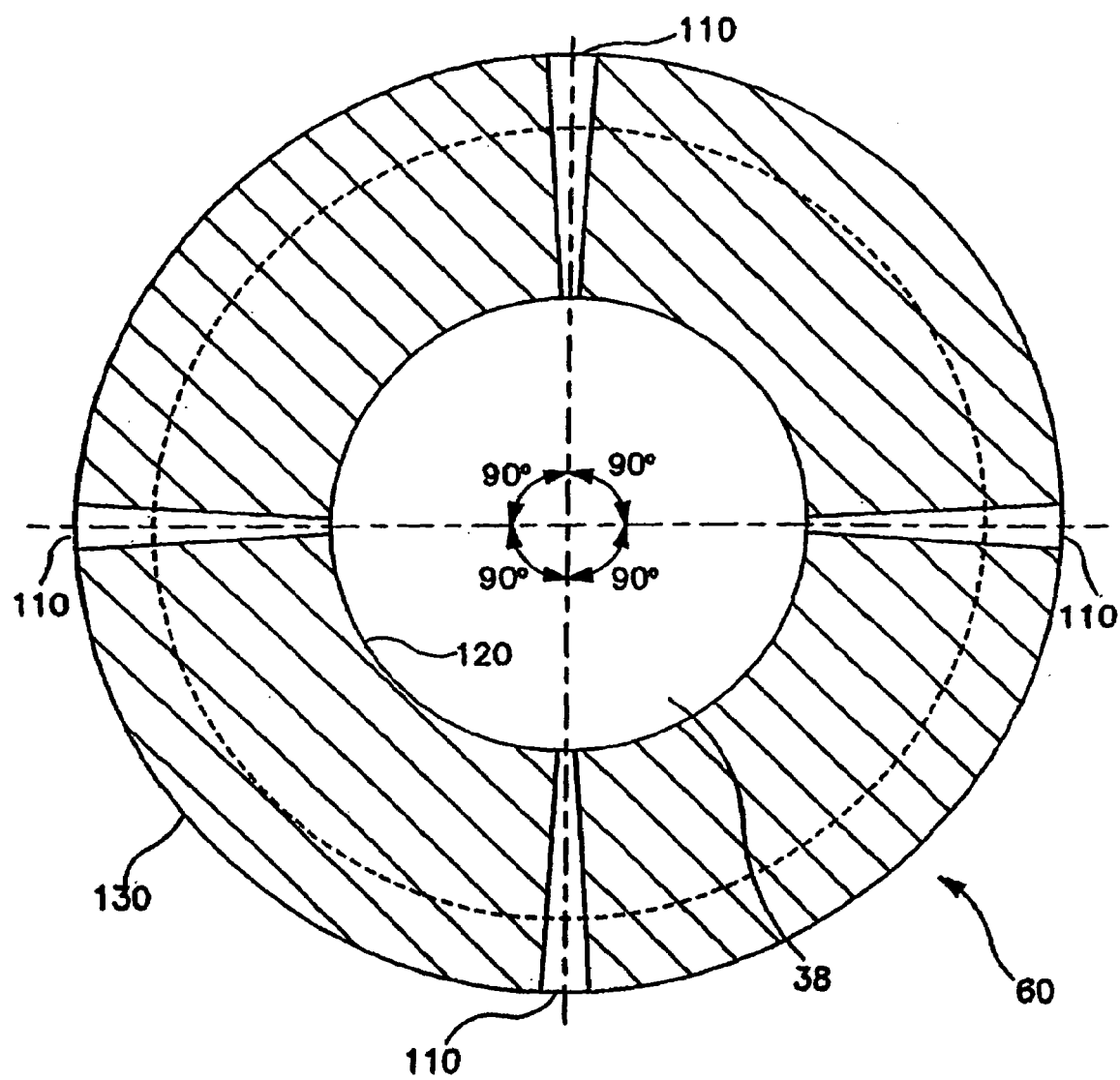
FIG. 6 is a cross section view of one embodiment of a diffuser of the present invention taken from its distal end, which illustrates openings that are tapered as they extend from the outside diameter of the diffuser to the inside diameter of the diffuser.
Figure 7:
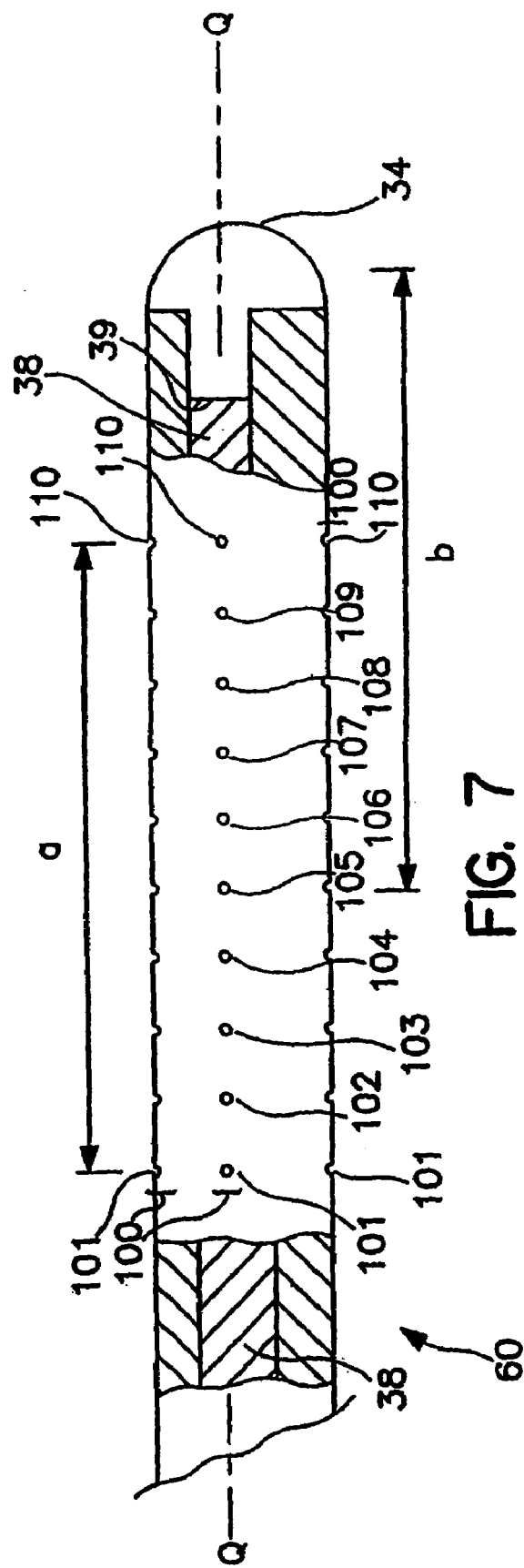
FIG. 7 is a side view of one embodiment of the diffuser of the present invention.

FIG. 6 is a cross section view of one preferred embodiment of a drug delivery segment (i.e. diffuser) 60 of the present invention taken from lumen distal end 39 of lumen 38 as shown in FIG. 7. The drug delivery segment is implantable in a patient for long periods of time (i.e., exceeding more than 24 hours), and is particularly useful for implantable drug delivery devices and systems to treat chronic disorders. The drug delivery segment described herein prevents soft tissue from entering the tubes and blocking flow of the fluid from the drug delivery segment to the target site within a patient. The drug delivery segment 60 has an inside surface 120 and an oustside surface 130. In preferred embodiment, durg delivery segment has a longitudinal length of about 0.1–1.0 cm, and more preferably about 0.5 cm. In a preferred embodiment, the inside diameter of diffuser 60 is about 0.032 inches (0.0812 cm), and the outside diameter of diffuser 60 is about 0.064 inches (0.1625 cm). In this preferred embodiment, tubes 101 through 110 extend radially from the inside diameter of diffuser 60 to the outside diameter of diffuser 60. In this embodiment, the length of the tubes 101 through 110 is about 0.016 inches (0.0406 cm). Preferably, the ratio of tube length to tube diameter of tubes 101 through 110 is about 5–25, and more preferably about 5.0. A benefit of the ratio of 5–25 of tube length to tube diameter is that flow resistance is provided, thereby permitting more equal flow between the most distal tube and the most proximal tube and thus assisting in the diffuser function. One way to obtain this tube structure is to use a laser or ion beam to drill tubes 101 through 110. In one preferred embodiment, tubes 101 through 110 have substantially the same diameter.

As shown in FIG. 6, tubes 110 can be tapered as they extend from the outside diameter of diffuser 60 to the inside diameter of diffuser 60. Lumen 38 extends along thelongitudinal axis Q—Q of diffuser 60. In a preferred embodiment, all of the tubes 101 through 110 (shown in FIG. 7) have the same shape as they extend from the outside diameter of diffuser 60 to the inside diameter of diffuser 60. While tubes 110 are shown as being tapered in FIG. 7, they can also be non-tapered, or can have tapered and non-tapered sections.

As previously described in connection with FIG. 3B, the opening defined by the distal end of the medical catheter can be a side opening. When the opening defined by the distal end of the catheter is a side opening, the drug delivery segment can cover the opening. In this alternative embodiment, the drug delivery segment does not define a lumen along its longitudinal axis, but still has tubes that extend radially from the outside surface of the drug delivery segment to the inside surface of the drug delivery segment, wherein the ratio of the length of the tubes to the diameter of the tubes is about 5–25. Further, any pattern of tubes can be used in connection with the present invention, including but not limited to, a pattern corresponding to the shape and/or location of an intended target site within a patient, e.g., a tumor.

FIG. 7 is a side view of one preferred embodiment of the drug delivery segment (i.e. diffuser) 60 of the present invention. In a preferred embodiment, the diffuser 60 comprises at least one row 100 parallel to the longitudinal axis Q—Q of diffuser 60. In the embodiment shown in FIG. 7, there are four rows 100 of tubes 101 through 110 extending along an axis parallel to the longitudinal axis Q—Q of diffuser 60. In this preferred embodiment, there are ten tubes per row 100. Preferably, the tubes in each row are equally spaced from each adjacent tube in the same row 100. As shown in FIG. 7, tube 101 is the most proximal hole, and tube 110 is the most distal tube, and tube 105 is the middle-tube. As shown in FIGS. 6 and 7, each row is about 90 degrees from each adjacent row along the outside diameter of diffuser 60 (as FIG. 7 is a side view, only three rows 100 of tubes 101 through 110 are shown). In FIG. 7, the distance from the most proximal tube 101 to the most distal tube 110 is identified as distance "a", and the distance from the middle tube 105 to about the mid-point of catheter tip 34 is identified as distance "b". In a preferred embodiment, the distance from the most proximal tube 101 to the most distal tube 110 is about 5.5 millimeters, and the distance from middle-tube 105 to about the mid-point of catheter tip 34 is about 5.0 millimeters.

Those of skill in the art will recognize that the above preferred embodiment can be modified without departing from the scope of the present invention. For example, eight (8) rows can be used instead of four (4) rows, wherein each row is about 45 degrees from each adjacent row along the outside surface 130 of the drug delivery segment 60. Each of the eight rows can have ten (10) tubes 101 through 110, for a total of eighty (80) tubes.

The key factors in obtaining relatively equal flow through each of the tubes 101 through 110, are as follows: (1) tube length relative to tube diameter; (2) number of tubes; and (3) an internal diameter of the diffuser 60 that is relatively large enough to provide fluid to the most distal tube 110. Those of skill in the art will readily recognize how to vary these factors as may be desired for a given flow rate.

The above described embodiment is particularly useful for implantable medical catheters wherein the drug delivery segment is implantable for more than twenty-four hours to provide fluid containing a therapeutic drug to a target site in a patient at flow rates of about 2 microliters/hour to 10 microliters/minute.

Fluid Restrictor—To balance the flow into each hemisphere of the patient's brain, resistance to fluid flow in each leg of the catheter must be significant compared to the resistance at the tissue interface. If the restrictor creates a pressure drop of about 2–10 psi for a flow rate of about 10 microliters/minute, variation in interstitial pressure (less than 0.5 psi) will not create an imbalance of flow in the two catheter legs for a desired flow rate of about 1–10 microliters/minute. For this pressure drop, the material for the restrictor must be very tortuous and have a significant length (i.e., thickness). For the restrictor material, a permeability constant of less than about 5,000 and a bubble point of less than about 10 psi is preferred. Since the restrictor is separated from the diffuser in this embodiment, the dimensions and materials are not limited to those typically considered acceptable for intraparenchymal implant. Acceptable materials for restrictors given the larger lengths possible outside the brain are sintered porous metals, and sintered and/or porous polymers. Methods of manufacture and materials for the restrictors of the present invention include, but are not limited to, thin sheet filter (e.g., polyethersulfone or polypropylene, from Pall Corporation (East Hills, N.Y.)), polycarbonate membrane (from Osmonics, Inc. (Minnetonka, Minn.)), polyvinylidine fluoride from Millipore Corporation (Bedford, Mass.)), depth filters from sintered metal (from Mott, Inc. (Farmington, Conn.)), sintered polyethylene (from Porex Surgical (College Park)), sintered glass (from Robu Glasfilter-Gerate GmbH (Hattert, Germany)), orifice sapphire, and/or capillary tubes. Preferably, the restrictor is a depth filter since it does not have disadvantages that the other materials may have. Sheet membranes have a disadvantage in that they have very small pores that may be prone to clogging and require a high pressure to pass air through the wet membrane (i.e., bubble point). Orifice-type restrictors have the disadvantage of pressure drop that is extremely sensitive to diameter, thereby making it difficult and expensive to match two restrictors of this type to achieve substantially equal flow.

The restrictor should provide a large pressure drop. The pressure drop can be expressed by Darcy's Law. Darcy's Law is as follows:

$$K = \frac{-F\mu T}{A \cdot \text{delta } P}$$

where K=permeability constant
   F=flow rate
   $\mu$=viscosity for the fluid
   T=thickness of porous path
   A=surface area
   delta P=pressure delta The conflicting requirements of the large surface area for a diffuser and a large pressure drop for the restrictor can be met by having separate structure for each of these functions.

Separating the restrictors from the diffusers, and placing the restrictors up stream of the diffusers results in the resistance to flow at the distal ends to be insignificant to the overall resistance to flow, and the fluid flow through multiple catheters is substantially equal.

An example is that for a "Y" catheter, if the resistance to flow through a first diffuser has a relative value of 1, and the resistance to flow through a second diffuser has a relative value of 2, then twice as much flow will go through the first diffuser.

On the other hand, if restrictors with a relative resistance value of 100 are placed up stream of the first and second diffusers, so that the overall resistance to flow through the first diffuser has a relative value of 101, and the overall resistance to flow through a second diffuser has a relative value of 102, then the flow through the first and second diffusers will be substantially equal. Equal restriction of fluid flow through each leg is the key to substantially equal fluid flow through each leg.

The features provided by this embodiment include:
1. Separate diffuser and restrictor features for bilateral intraparenchymal drug delivery catheter.
2. Use of simple diffusers that have insufficient tortuosity of the porous structure to make acceptable restrictors.
3. Use of multiple small holes (less than 0.005 inches in diameter; created with a laser) as a fluid diffuser.
4. Location of catheter restrictor at proximal end (not distal) of catheter to provide greater device flexibility, i.e., reduce the number of joint, bonds, components for distal catheter segment.
5. Capability to control flow in the brain catheter with changes in catheter design/materials not directly implanted in the brain tissues.

Thus, the present invention provides for multiple catheter ends for drug delivery. More specifically, the present invention provides for multiple catheter ends, e.g. at least two, into the brain of patient, and even more specifically, into the two different hemispheres of the brain, with each catheter end supplied with therapeutic drugs by the same pump, and with the fluid flow of the therapeutic agent being substantially equal between the two catheter ends.

The present invention also provides a catheter to diffuse a therapeutic agent over a large surface area than from a single point source. The benefits of this structure is that it decreases the fluid flux and reduces the change of damaging patient tissue. In order for equal or near equal bilateral drug delivery to occur, two catheters are required. It is usually desirable to have equal flow in both catheters to deliver equal amounts of drug to both brain hemispheres.

The present invention can be used for many drug delivery applications, including but not limited to intraparenchymal tissue delivery, intrathecal drug delivery, and intra-cerebral ventricular (ICV) drug delivery.

Many modifications and variations may be made in the techniques and structures described and illustrated herein without departing from the spirit and scope of the present invention. For example, the present invention can be used to infuse a cytostatic agent into a malignant mass located in a variety of places in the body, or infuse a nerve growth factor into the intrathecal space of the spinal column, or to treat Alzheimer's disease by infusing indomethacin or other drug into a patient's hippocampus. Accordingly, the techniques and structures described and illustrated herein should be understood to be illustrative only and not limiting upon the scope of the present invention.

The invention claimed is:

1. A medical catheter comprising:
   a lumen comprising a proximal end and a downstream direction leading away from the proximal end;
   a connector located distal from the proximal end of the lumen, the connector separating the lumen into two or more legs downstream from the connector;
   at least one opening located in each leg of the two or more legs, wherein the at least one opening in each leg is located downstream from the connector, and wherein a therapeutic drug can be delivered out of the catheter through the opening to a targeted patient site; and
   a flow restrictor located within each leg of the two or more legs, wherein the at least one opening in each leg is located downstream from the flow restrictor.

2. A medical catheter according to claim 1, wherein the flow restrictor comprises radiopaque material.

3. A medical catheter according to claim 1, wherein the flow restrictor comprises sintered metal microspheres.

4. A medical catheter according to claim 1, wherein the flow restrictor comprises metal selected from the group consisting of tungsten, tantalum, and titanium.

5. A medical catheter according to claim 1, wherein the flow restrictor comprises pores ranging in diameter from about 0.3 to 6.2 microns.

6. A medical catheter according to claim 1, further comprising a diffuser proximate each opening of the at least one opening, wherein the therapeutic drug passes through the diffuser to reach the targeted patient site.

7. A medical catheter according to claim 6, wherein the diffuser comprises radiopaque material.

8. A medical catheter according to claim 6, wherein the diffuser comprises sintered metal microspheres.

9. A medical catheter according to claim 6, wherein the diffuser comprises metal selected from the group consisting of tungsten, tantalum, and titanium.

10. A medical catheter according to claim 6, wherein the diffuser comprises pores ranging in diameter from about 0.3 to 6.2 microns.

11. A medical catheter according to claim 6, wherein the diffuser comprises a plurality of holes formed in a wall.

12. A medical catheter according to claim 1, wherein the at least one opening in at least one leg of the two or more legs comprises a side opening.

13. A medical catheter according to claim 12, wherein the at least one leg comprising a side opening comprises a distal tip downstream from the side opening.

14. A medical catheter according to claim 1, further comprising a flow restrictor located upstream from the two or more legs.

15. A medical catheter comprising:
   a lumen comprising a proximal end and a downstream direction leading away from the proximal end;
   a connector located distal from the proximal end of the lumen, the connector separating the lumen into two or more legs downstream from the connector;
   at least one opening located in each leg of the two or more legs, wherein the at least one opening is located downstream from the connector, and wherein a therapeutic drug can be delivered out of the catheter through the at least one opening to a targeted patient site; and
   a flow restrictor located within each leg of the two or more legs, wherein the at least one opening in each leg is located downstream from the flow restrictor;
   wherein overall resistance to flow from the proximal end of the lumen to the at least one opening in each leg of the two or more legs is substantially equal.

16. A medical catheter according to claim 15, wherein the flow restrictor comprises radiopaque material.

17. A medical catheter according to claim 15, wherein the flow restrictor comprises sintered metal microspheres.

18. A medical catheter according to claim 15, wherein the flow restrictor comprises metal selected from the group consisting of tungsten, tantalum, and titanium.

19. A medical catheter according to claim 15, wherein the flow restrictor comprises pores ranging in diameter from about 0.3 to 6.2 microns.

20. A medical catheter according to claim 15, further comprising a diffuser proximate the at least one opening in each leg, wherein the therapeutic drug passes through the diffuser to reach the targeted patient site.

21. A medical catheter according to claim 20, wherein the diffuser comprises radiopaque material.

22. A medical catheter according to claim 20, wherein the diffuser comprises sintered metal microspheres.

23. A medical catheter according to claim 20, wherein the diffuser comprises metal selected from the group consisting of tungsten, tantalum, and titanium.

24. A medical catheter according to claim 20, wherein the diffuser comprises pores ranging in diameter from about 0.3 to 6.2 microns.

25. A medical catheter according to claim 20, wherein the diffuser comprises a plurality of holes formed in a wall.

26. A medical catheter according to claim 15, wherein the at least one opening in at least one leg of the two or more legs comprises a side opening.

27. A medical catheter according to claim 26, wherein the at least one leg comprising a side opening comprises a distal tip downstream from the side opening.

28. A medical catheter according to claim 15, further comprising a flow restrictor located upstream from the two or more legs.

29. A medical catheter comprising;
   a lumen that comprises a proximal end and a downstream direction leading away from the proximal end, wherein the lumen separates into two or more legs downstream from the proximal end;
   at least one opening located in each leg of the two or more legs, wherein a therapeutic drug can be delivered out of the catheter through the at least one opening to a targeted patient site; and
   a flow restrictor located within each leg of the two or more legs;
   wherein overall resistance to flow from the proximal end of the lumen to the at least one opening in each leg of the two or more legs is substantially equal.

30. A medical catheter according to claim 29, wherein the at least one opening in at least one leg of the two or more legs is located downstream from the flow restrictor in the at least one leg.

31. A medical catheter according to claim 29, wherein the flow restrictor comprises radiopaque material.

32. A medical catheter according to claim 29, wherein the flow restrictor comprises sintered metal microspheres.

33. A medical catheter according to claim 29, wherein the flow restrictor comprises metal selected from the group consisting of tungsten, tantalum, and titanium.

34. A medical catheter according to claim 29, wherein the flow restrictor comprises pores ranging in diameter from about 0.3 to 6.2 microns.

35. A medical catheter according to claim 29, further comprising a diffuser proximate each opening of the at least one opening, wherein the therapeutic drug passes through the diffuser to reach the targeted patient site.

36. A medical catheter according to claim 35, wherein the diffuser in at least one leg of the two or more legs is located downstream from the flow restrictor in the at least one leg.

37. A medical catheter according to claim 35, wherein the diffuser comprises radiopaque material.

38. A medical catheter according to claim 35, wherein the diffuser comprises sintered metal microspheres.

39. A medical catheter according to claim 35, wherein the diffuser comprises metal selected from the group consisting of tungsten, tantalum, and titanium.

40. A medical catheter according to claim 35, wherein the diffuser comprises pores ranging in diameter from about 0.3 to 6.2 microns.

41. A medical catheter according to claim 35, wherein the diffuser comprises a plurality of holes formed in a wall.

42. A medical catheter according to claim 29, wherein the at least one opening in at least one leg of the two or more legs comprises a side opening.

43. A medical catheter according to claim 42, wherein the at least one leg comprising a side opening comprises a distal tip downstream from the side opening.

44. A medical catheter according to claim 29, further comprising a flow restrictor located upstream from the two or more legs.

45. A medical catheter comprising;
   a lumen that comprises a proximal end and a downstream direction leading away from the proximal end, wherein the lumen separates into two or more branches at a first location downstream from the proximal end, and wherein at least one branch of the two or more branches separates into two or more legs downstream from the first location;
   at least one opening located in each leg of the two or more legs, wherein a therapeutic drug can be delivered out of the catheter through the at least one opening to a targeted patient site; and
   a flow restrictor located within each leg of the two or more legs.

46. A medical catheter according to claim 45, wherein overall resistance to flow from the proximal end of the lumen to the at least one opening in each leg of the two or more legs is substantially equal.

47. A medical catheter according to claim 45, further comprising a flow restrictor located upstream from the two or more branches.

48. A medical catheter according to claim 45, further comprising a flow restrictor located upstream from the two or more legs in at least one branch of the two or more branches.

49. A medical catheter according to claim 45, wherein the at least one opening in at least one leg of the two or more legs is located downstream from the flow restrictor in the at least one leg.

50. A medical catheter according to claim 45, wherein the flow restrictor comprises radiopaque material.

51. A medical catheter according to claim 45, wherein the flow restrictor comprises sintered metal microspheres.

52. A medical catheter according to claim 45, wherein the flow restrictor comprises metal selected from the group consisting of tungsten, tantalum, and titanium.

53. A medical catheter according to claim 45, wherein the flow restrictor comprises pores ranging in diameter from about 0.3 to 6.2 microns.

54. A medical catheter according to claim 45, further comprising a diffuser proximate each opening of the at least one opening, wherein the therapeutic drug passes through the diffuser to reach the targeted patient site.

55. A medical catheter according to claim 54, wherein the diffuser in at least one leg of the two or more legs is located downstream from the flow restrictor in the at least one leg.

56. A medical catheter according to claim 54, wherein the diffuser comprises radiopaque material.

57. A medical catheter according to claim 54, wherein the diffuser comprises sintered metal microspheres.

58. A medical catheter according to claim 54, wherein the diffuser comprises metal selected from the group consisting of tungsten, tantalum, and titanium.

59. A medical catheter according to claim 54, wherein the diffuser comprises pores ranging in diameter from about 0.3 to 6.2 microns.

60. A medical catheter according to claim 54, wherein the diffuser comprises a plurality of holes formed in a wall.

61. A medical catheter according to claim 45, wherein the at least one opening in at least one leg of the two or more legs comprises a side opening.

62. A medical catheter according to claim 61, wherein the at least one leg comprising a side opening comprises a distal tip downstream from the side opening.

* * * * *